(12) United States Patent
Norman et al.

(10) Patent No.: US 6,287,826 B1
(45) Date of Patent: Sep. 11, 2001

(54) ENZYMATIC PREPARATION OF GLUCOSE SYRUP FROM STARCH

(75) Inventors: Barrie Edmund Norman, Birkerød; Hanne Vang Hendriksen, Holte, both of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/264,097

(22) Filed: Mar. 8, 1999

Related U.S. Application Data
(60) Provisional application No. 60/079,209, filed on Mar. 24, 1998.

(30) Foreign Application Priority Data

Mar. 9, 1998 (DK) .................................................. 0321/98

(51) Int. Cl.[7] .............................. C12P 19/14; C08B 31/00
(52) U.S. Cl. .............................. 435/99; 435/98; 536/102; 536/103
(58) Field of Search ........................ 439/99, 98; 536/102, 536/103

(56) References Cited

U.S. PATENT DOCUMENTS
3,922,196 * 11/1975 Leach et al. ........................... 435/99

FOREIGN PATENT DOCUMENTS
WO 96/23874 * 8/1996 (WO).
WO 97/41213 * 11/1997 (WO).

* cited by examiner

Primary Examiner—Francisco Prats
(74) Attorney, Agent, or Firm—Elias J. Lambiris, Esq.

(57) ABSTRACT

The present invention relates to a process for the preparation of a glucose syrup wherein starch is treated with a Termamyl-like α-amylase comprising a substitution in Val54 shown in SEQ ID NO: 2 or in the corresponding position in another Termamyl-like α-amylase. The invention also relates to a glucose syrup obtainable by the process of the invention and the use thereof as ingredient in food products. An object of the invention is also to provide for the use of a Termamyl-like α-amylase with a substitution in position Val54 using SEQ ID NO: 2 as the backbone or a corresponding position in another Termamyl-like α-amylase for preparing glucose syrup.

16 Claims, 6 Drawing Sheets

```
       1                                                                    50
1   HHNGTNGTMM  QYFEWHLPND  GNHWNRLRDD  ASNLRNRGIT  AIWIPPAWKG
2   ..NGTNGTMM  QYFEWYLPND  GNHWNRLRSD  ASNLKDKGIS  AVWIPPAWKG
3   HHNGTNGTMM  QYFEWYLPND  GNHWNRLRDD  AANLKSKGIT  AVWIPPAWKG
4   ....VNGTLM  QYFEWYTPND  GQHWKRLQND  AEHLSDIGIT  AVWIPPAYKG
5   ..ANLNGTLM  QYFEWYMPND  GQHWRRLQND  SAYLAEHGIT  AVWIPPAYKG
6   .AAPFNGTMM  QYFEWYLPDD  GTLWTKVANE  ANNLSSLGIT  ALWLPPAYKG 51                                                                  100
1   TSQNDVGYGA  YDLYDLGEFN  QKGTVRTKYG  TRSQLESAIH  ALKNNGVQVY
2   ASQNDVGYGA  YDLYDLGEFN  QKGTIRTKYG  TRNQLQAAVN  ALKSNGIQVY
3   TSQNDVGYGA  YDLYDLGEFN  QKGTVRTKYG  TRNQLQAAVT  SLKNNGIQVY
4   LSQSDNGYGP  YDLYDLGEFQ  QKGTVRTKYG  TKSELQDAIG  SLHSRNVQVY
5   TSQADVGYGA  YDLYDLGEFH  QKGTVRTKYG  TKGELQSAIK  SLHSRDINVY
6   TSRSDVGYGV  YDLYDLGEFN  QKGTVRTKYG  TKAQYLQAIQ  AAHAAGMQVY 101                                                                 150
1   GDVVMNHKGG  ADATENVLAV  EVNPNNRNQE  ISGDYTIEAW  TKFDFPGRGN
2   GDVVMNHKGG  ADATEMVRAV  EVNPNNRNQE  VSGEYTIEAW  TKFDFPGRGN
3   GDVVMNHKGG  ADGTEIVNAV  EVNRSNRNQE  TSGEYAIEAW  TKFDFPGRGN
4   GDVVLNHKAG  ADATEDVTAV  EVNPANRNQE  TSEEYQIKAW  TDFRFPGRGN
5   GDVVINHKGG  ADATEDVTAV  EVDPADRNRV  ISGEHLIKAW  THFHFPGRGS
6   ADVVFDHKGG  ADGTEWVDAV  EVNPSDRNQE  ISGTYQIQAW  TKFDFPGRGN 151                                                                 200
1   TYSDFKWRWY  HFDGVDWDQS  RQFQNRIYKF  RGDGKAWDWE  VDSENGNYDY
2   THSNFKWRWY  HFDGVDWDQS  RKLNNRIYKF  RGDGKGWDWE  VDTENGNYDY
3   NHSSFKWRWY  HFDGTDWDQS  RQLQNKIYKF  RGTGKAWDWE  VDTENGNYDY
4   TYSDFKWHWY  HFDGADWDES  RKI.SRIFKF  RGEGKAWDWE  VSSENGNYDY
5   TYSDFKWHWY  HFDGTDWDES  RKL.NRIYKF  ..QGKAWDWE  VSNENGNYDY
6   TYSSFKWRWY  HFDGVDWDES  RKL.SRIYKF  RGIGKAWDWE  VDTENGNYDY
```

Fig. 4A

```
      201                                                                250
1    LMYADVDMDH PEVVNELRRW GEWYTNTLNL DGFRIDAVKH IKYSFTRDWL
2    LMYADIDMDH PEVVNELRNW GVWYTNTLGL DGFRIDAVKH IKYSFTRDWS
3    LMYADVDMDH PEVIHELRNW GVWYTNTLNL DGFRIDAVKH IKYSFTRDWL
4    LMYADVDYDH PDVVAETKKW GIWYANELSL DGFRIDAAKH IKFSFLRDWV
5    LMYADIDYDH PDVAAEIKRW GTWYANELQL DGFRLDAVKH IKFSFLRDWV
6    LMYADLDMDH PEVVTELKNW GKWYVNTTNI DGFRLDAVKH IKFSFFPDWL 251                                                                300
1    THVRNATGKE MFAVAEFWKN DLGALENYLN KTNWNHSVFD VPLHYNLYNA
2    IHVRSATGKN MFAVAEFWKN DLGAIENYLN KTNWNHSVFD VPLHYNFYNA
3    THVRNTTGKP MFAVAEFWKN DLGAIENYLN KTSWNHSAFD VPLHYNLYNA
4    QAVRQATGKE MFTVAEYWQN NAGKLENYLN KTSFNQSVFD VPLHFNLQAA
5    NHVREKTGKE MFTVAEYWQN DLGALENYLN KTNFNHSVFD VPLHYQFHAA
6    SYVRSQTGKP LFTVGEYWSY DINKLHNYIT KTDGTMSLFD APLHNKFYTA 301                                                                350
1    SNSGGNYDMA KLLNGTVVQK HPMHAVTFVD NHDSQPGESL ESFVQEWFKP
2    SKSGGNYDMR QIFNGTVVQR HPMHAVTFVD NHDSQPEEAL ESFVEEWFKP
3    SNSGGYYDMR NILNGSVVQK HPTHAVTFVD NHDSQPGEAL ESFVQQWFKP
4    SSQGGGYDMR RLLDGTVVSR HPEKAVTFVE NHDTQPGQSL ESTVQTWFKP
5    STQGGGYDMR KLLNGTVVSK HPLKSVTFVD NHDTQPGQSL ESTVQTWFKP
6    SKSGGAFDMR TLMTNTLMKD QPTLAVTFVD NHDTEPGQAL QSWVDPWFKP 351                                                                400
1    LAYALILTRE QGYPSVFYGD YYGIPTHS.. .VPAMKAKID PILEARQNFA
2    LAYALTLTRE QGYPSVFYGD YYGIPTHG.. .VPAMKSKID PILEARQKYA
3    LAYALVLTRE QGYPSVFYGD YYGIPTHG.. .VPAMKSKID PLLQARQTFA
4    LAYAFILTRE SGYPQVFYGD MYGTKGTSPK EIPSLKDNIE PILKARKEYA
5    LAYAFILTRE SGYPQVFYGD MYGTKGDSQR EIPALKHKIE PILKARKQYA
6    LAYAFILTRQ EGYPCVFYGD YYGIPQYN.. .IPSLKSKID PLLIARRDYA 401                                                                450
1    YGTQHDYFDH HNIIGWTREG NTTHPNSGLA TIMSDGPGGE KWMYVGQNKA
2    YGRQN..... .......... .......... .......... ..........
3    YGTQHDYFDH HDIIGWTREG NSSHPNSGLA TIMSDGPGGN KWMYVGKNKA
4    YGPQHDYIDH PDVIGWTREG DSSAAKSGLA ALITDGPGGS KRMYAGLKNA
5    YGAQHDYFDH HDIVGWTREG DSSVANSGLA ALITDGPGGA KRMYVGRQNA
6     YGTQHDYLDH SDIIGWTREG GTEKPGSGLA ALITDGPGGS KWMYVGKQHA
```

Fig. 4B

```
    451                                                              500
1   GQVWHDITGN KPGTVTINAD GWANFSVNGG SVSIWVKR.. ..........
2   .......... .......... .......... .......... ..........
3   GQVWRDITGN RTGTVTINAD GWGNFSVNGG SVSVWVKQ.. ..........
4   GETWYDITGN RSDTVKIGSD GWGEFHVNDG SVSIYVQ... ..........
5   GETWHDITGN RSEPVVINSE GWGEFHVNGG SVSIYVQR.. ..........
6   GKVFYDLTGN RSDTVTINSD GWGEFKVNGG SVSVWVPRKT TVSTIARPIT 501                 519
1   .......... .........
2   .......... .........
3   .......... .........
4   .......... .........
5   .......... .........
6   TRPWTGEFVR WTEPRLVAW
```

Fig. 4C

ENZYMATIC PREPARATION OF GLUCOSE SYRUP FROM STARCH

CROSS-REFERENCE TO RELATED APPLICATIONS

This application claims priority under U.S.C. 119 of Danish application 0321/98 filed Mar. 9, 1998 and U.S. provisional application 60/079,209 filed Mar. 24, 1998, the contents of which are fully incorporated herein by reference.

FIELD OF THE INVENTION

The present invention relates to a process for the preparation of starch-hydrolysate syrups having characteristics which render them particularly attractive for a variety of industrial applications, notably in the food industry. The invention makes it possible using one enzyme, for the first time, to obtain syrups of the above-mentioned kind which closely match syrups whose preparation previously only feasible using acid hydrolysis (i.e., non-enzymatic hydrolysis) of starch.

BACKGROUND OF THE INVENTION

Glucose syrups with a DE (Dextrose Equivalent) around 42 is widely used in industry as an ingredient in products such as hard boiled candy, toffees, fudge, fondant and the like.

Traditionally 42 DE glucose syrups are produced by standard acid conversion. A starch slurry is initially acidified to pH 2, and is then pumped into a continuous reactor which operates at elevated temperature and pressure. After a period of time the liquor is returned to atmospheric conditions, neutralised, clarified, decolourised and concentrated to the final syrup. Such acid converted glucose syrup profile shown in FIG. 1 reduce the tendency of sucrose to crystallise, they slow down the tendency to shell-graining and they contribute to the characteristic "mouth-feel".

Today also enzymatic conversion of starch into glucose syrup has been suggested. However, such glucose syrups typically have a sugar spectrum which is quite different from the traditionally used 42 DE acid converted glucose syrup.

SUMMARY OF THE INVENTION

The present invention is based on the finding that a glucose syrup with a DE in the range from 35 to 45 having a sugar spectrum close to that of the traditionally acid converted 42 DE glucose syrup can be obtained by treating starch with a 54W substituted variant of Termamyl® (which is a commercially available *Bacillus licheniformis* α-amylase).

In the first aspect the invention relates to a process for the preparation of a glucose syrup wherein starch is treated with a Termamyl-like α-amylase comprising a substitution in Val54 shown in SEQ ID NO: 2 or in the corresponding position in another Termamyl-like α-amylase.

The invention also relates to a glucose syrup obtainable by the process of the invention. Further, an aspect the invention also relates to the use of said glucose syrup obtainable by the process of the invention as ingredient in food products such as hard boiled candy, toffees, fudge, fondant and the like.

Another object of the invention is to provide for the use of a Termamyl-like α-amylase with a substitution in position Val54 using SEQ ID NO: 2 as the backbone (i.e., parent enzyme) or a corresponding position in another Termamyl-like α-amylase for preparing glucose syrup.

BRIEF DESCRIPTION OF THE DRAWINGS

FIG. 4A–4C is an alignment of the amino acid sequences of six parent Termamyl-like α-amylases. The numbers on the Extreme left designate the respective amino acid sequences as follows:
1: Bacillus sp. α-amylase, (SEQ ID NO: 5)
2: Kaoamyl α-amylase), (SEQ ID NO: 6)
3: Bacillus sp. α-amylase, (SEQ ID NO: 7)
4: *B. amyloliquefaciens* α-amylase(BAN) (SEQ ID NO: 3),
5: *Bacillus licheniformis* α-amylase (SEQ ID NO: 2),
6: α-amylase disclosed in Tsukamoto et al., Biochemical and Biophysical Research Communications, 151 (1988), pp. 25–31 (SEQ ID NO: 8).

DETAILED DESCRIPTION OF THE INVENTION

The present invention is based on the finding that a novel glucose syrup with a DE in the range from 35 to 45 having a sugar spectrum and properties close to that of the traditionally acid converted glucose syrup, often referred to as "42 DE glucose syrup" is obtained by treating starch with a Val54Trp (V54W) substituted variants of the commercially available *Bacillus licheniformis* α-amylase, sold under the trade name Termamyl® (Novo Nordisk). The DNA and protein sequence of Termamyl® is displayed in SEQ ID NO: 1 and 2, respectively.

Substitution in the Val54 position of Termamyl-like α-amylase, including the *B. licheniformis* α-amylase, is known from WO 97/41213 (Novo Nordisk). However, it is surprising that a Val54 substituted variant can be used to preparing a syrup from starch having a sugar spectrum which is close to that of an acid converted 42 DE glucose syrup as a glucose syrup prepared from starch treated with parent *B. licheniformis* α-amylase (SEQ ID NO: 2) has a sugar spectrum quite different therefrom.

In the first aspect the invention relates to a glucose syrup (or speciality syrup) prepared by treating starch with the *Bacillus licheniformis* α-amylase shown in SEQ ID NO: 2 comprising a substitution in position Val54 or a Termamyl-like α-amylase (as defined below) substituted in a position corresponding to Val54 of SEQ ID NO: 2.

The glucose syrup of the invention has properties close to that of the traditional acid converted 42 DE syrups with regard to its sugar spectrum, i.e., composition of dextrose (DP1), maltose (DP2), maltotriose (DP3), maltotetraose (DP4), maltopentaose (DP5) and a number of higher sugars such as DP10 etc. The rheological properties, such as the viscosity, resembles the traditional acid converted DE 42 syrup much closer than a corresponding syrup prepared under the same conditions by treatment with parent *B. licheniformis* α-amylase (i.e., SEQ ID NO: 2).

Figure 1:
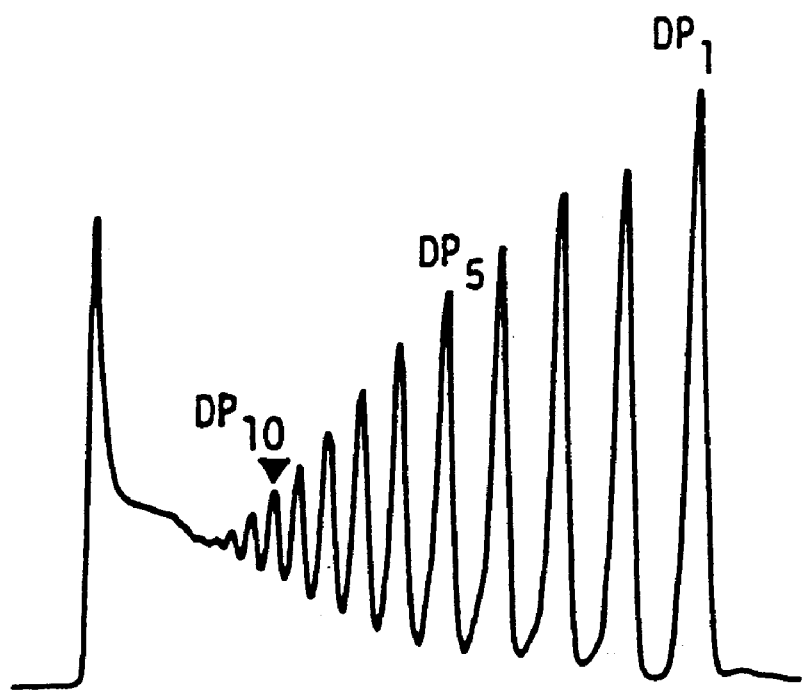
FIG. 1 shown the sugar spectrum of a 42 DE acid converted glucose syrup.
Figure 2:
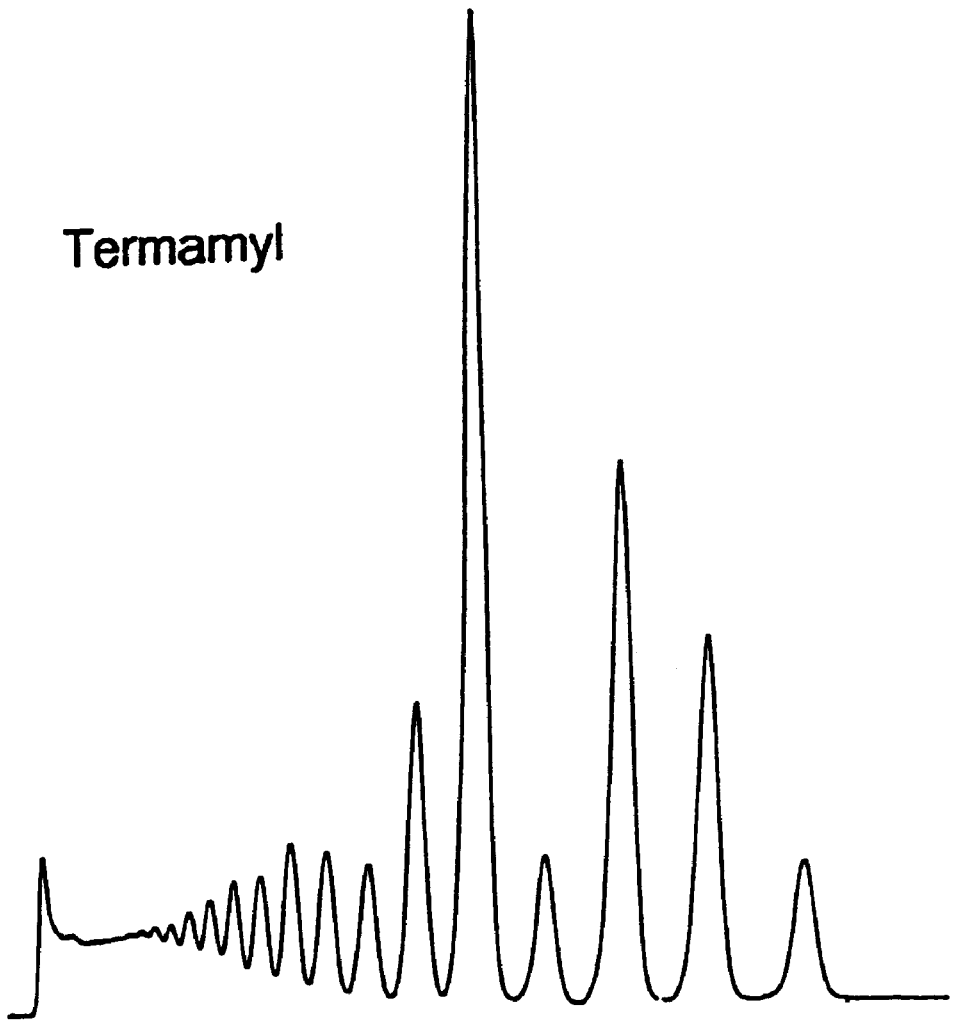
FIG. 2 shows the sugar spectrum of a Termamyl® (i.e., *Bacillus licheniformis* α-amylase from Novo Nordisk shown in SEQ ID NO: 2) converted glucose syrup.
Figure 3:
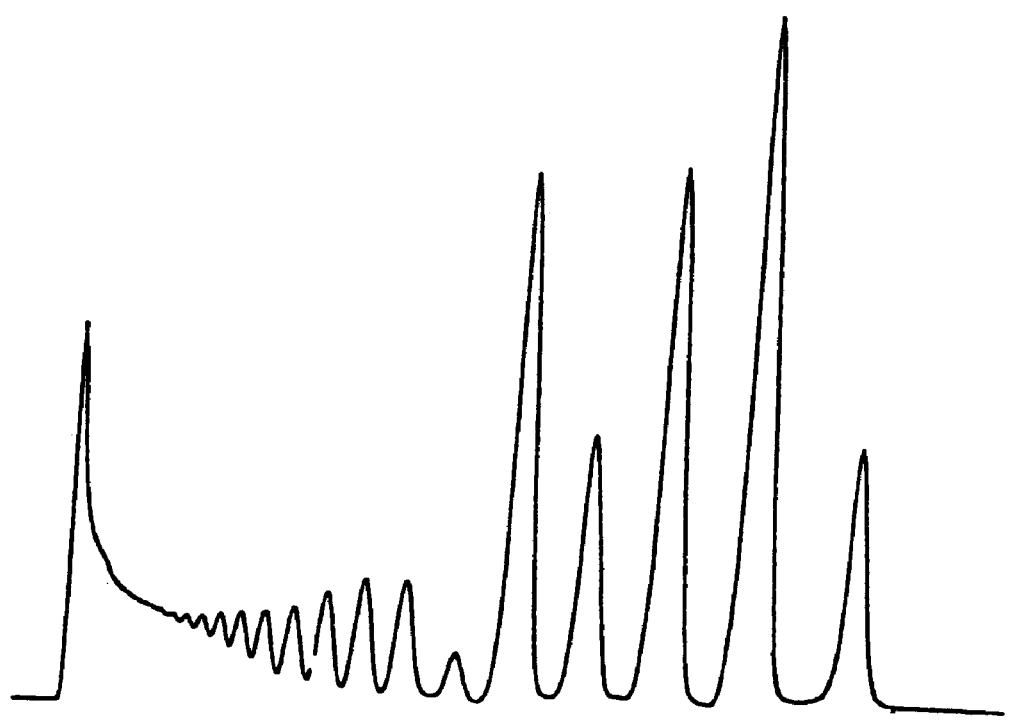
FIG. 3 shows the sugar spectrum of a V54W substituted *Bacillus licheniformis* α-amylase variant converted glucose syrup of the invention.

As can been seen clearly by comparing FIGS. 1 to 3 a glucose syrup prepared by treating starch with the Val54Trp substituted Termamyl variant (FIG. 3) has a sugar spectrum closer to that of the acid converted 42 DE syrup (FIG. 1) than that of the glucose syrup prepared using parent *B. licheniformis* α-amylase (FIG. 2).

By using the Val54 substituted *Bacillus licheniformis* α-amylase variant for preparing a glucose syrup of the invention it can be seen that especially the DP1 and DP4 sugar content has been increased to a level closer to that of the traditional 42 DE acid converted glucose syrup and the DP5 sugar content has been decreased to a level closer to that of the 42 DE glucose syrup in comparison to the corresponding glucose syrup prepared using parent *B. licheniformis* α-amylase. Further, the content of the higher sugars, as can be seen by comparing the peak(s) on the left side of FIGS. 1 to 3, are also increased to a level closer to that of the acid converted 42 DE glucose syrup in comparison to corresponding parent *B. licheniformis* α-amylase converted starch glucose syrup.

According to the invention only one enzyme need to be used for producing the glucose syrup of the invention, i.e. Val54 substituted Termamyl-like α-amylase.

The glucose syrup of the invention may be prepared by treating starch with a Val54 substituted Termamyl-like α-amylase variant for between 20 and 100 hours, preferably 50–80 hours, especially 60–75 hours at temperature in the range around 80–105° C. The pH should be in the range from pH 4–7, preferably from pH 4.5–6.5, especially around pH 5.5–6.2. To provide suitable conditions for Termamyl-like α-amylases, which generally seen have a high degree of Calcium dependency, from 20–60 ppm $Ca^{2+}$, preferably around 40 ppm $Ca^{2+}$ should be present in the reaction slurry.

Enzymatic conversion of starch into a glucose syrup of the acid converted 42 DE syrup type should have a number of advantages including:

enzymatic conversion is a mild process, reduction of the formation of colour precursor hydroxymethyl furfural, no formation of anhydroglucose as a by-product, lower ash content because of a reduction in the acid requirements, cheaper downstream processing and refining.

The Termamyl-like a-amylase

According to the invention the Termamyl-like variant may be any α-amylases produced by Bacillus spp. with a high degree of homology on the amino acid level to SEQ ID NO: 2 herein, as will be defined below.

A not exhaustive list of such enzymes are the following Bacillus sp. α-amylases:

*B. amyloliquefaciens* a-amylase disclosed in SEQ ID NO: 4 of WO 97/41213 which is about 89% homologous with the *B. licheniformis* α-amylase shown in SEQ ID NO: 2 below; the *B. stearothermophilus* a-amylase disclosed in SEQ ID NO: 6 in WO 97/41213. Further, homologous a-amylases include an α-amylase derived from a strain of the Bacillus sp. NCIB 12289, NCIB 12512, NCIB 12513 or DSM 9375, all of which are described in detail in WO 95/26397, and the a-amylase described by Tsukamoto et al., *Biochemical and BioPhysical Research Communications*, 151 (1988), pp. 25–31.

Other Bacillus sp. α-amylases contemplated according to the present invention to be within the definition of Termamyl-like α-amylases are the α-amylases disclosed in SEQ ID NO. 1, 2, 3 and 7 of WO 96/23873 and variants thereof, including specifically the ones described in WO 96/23873.

Variants and hybrids of the above mentioned Termamyl-like α-amylases are also contemplated.

In an embodiment of the invention the parent Termamyl-like α-amylase is a hybrid α-amylase of SEQ ID NO: 2 and SEQ ID NO: 4. Specifically, the parent hybrid Termamyl-like α-amylase may be identical to the Termamyl sequence, i.e., the *Bacillus licheniformis* α-amylase shown in SEQ ID NO: 2, except that the N-terminal 35 amino acid residues (of the mature protein) has been replaced by the N-terminal 33 residues of BAN (mature protein), i.e., the *Bacillus amyloliquefaciens* alpha-amylase shown in SEQ ID NO: 4 (the DNA sequence of the *Bacillus amyloliquefaciens* alpha-amylase is displayed in SEQ ID NO: 3), which further may have the following mutations: H156Y+A181T+N190F+A209V+Q264S (using the numbering in SEQ ID NO: 2). The hybrid may be constructed by SOE-PCR (Higuchi et al. 1988, Nucleic Acids Research 16:7351).

Still further Termamyl-like α-amylases include the α-amylase produced by the *B. licheniformis* strain described in EP 0,252,666 (ATCC 27811), and the α-amylases identified in WO 91/00353 and WO 94/18314. Other commercial Termamyl-like α-amylases are Optitherm™ and Takatherm™ (available from Solvay), Maxamyl™ (available from Gist-Brocades/Genencor), Spezyme AA™ and Spezyme Delta AA™ (available from Genencor), and Keistase™ (available from Daiwa).

Because of the substantial homology found between these a-amylases, they are considered to belong to the same class of a-amylases, namely the class of "Termamyl-like a-amylases".

Accordingly, in the present context, the term "Termamyl-like a-amylase" is also intended to indicate an a-amylase which, at the amino acid level, exhibits a substantial homology to the *B. licheniformis* a-amylase having the amino acid sequence shown in SEQ ID NO: 2 herein. In other words, a "Termamyl-like a-amylase" is an a-amylase which has the amino acid sequence shown in SEQ ID NO: 2 herein or any α-amylase which displays at least 60%, such as at least 70%, e.g., at least 75%, or at least 80%, e.g., at least 85%, at least 90% or at least 95% homology with SEQ ID NO; 2.

The "homology" may be determined by use of any conventional algorithm, preferably by use of the GAP programme from the GCG package version 7.3 (June 1993) using default values for GAP penalties, which is a GAP creation penalty of 3.0 and GAP extension penalty of 0.1, (Genetic Computer Group (1991) Programme Manual for the GCG Package, version 7, 575 Science Drive, Madison, Wis., USA 53711).

A structural alignment between Termamyl and a Termamyl-like α-amylase may be used to identify equivalent/corresponding positions in other Termamyl-like α-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEBS LETTERS 224, pp. 149–155) and reverse threading (Huber, T; Torda, AE, PROTEIN SCIENCE Vol. 7, No. 1 pp. 142–149 (1998).

In an embodiment of the invention the Termamyl-like α-amylase variant is one of the following *B. licheniformis* α-amylase variants (the parent *B. licheniformis* α-amylase is shown in SEQ ID NO: 2): V54A,R,D,N,C,E,Q,G,H,I,L,K, M,F,P,S,T,W,Y or a Termamyl-like α-amylase or variant (as defined above) with a substitution in a position corresponding to Val54 in SEQ ID NO: 2.

In a preferred embodiment the Termamyl-like α-amylase variant is one of the following substitutions *B. licheniformis* α-amylase variants with one of the following substitutions: V54W,Y or F or a Termamyl-like α-amylase variant with a substitution in a corresponding position.

Construction of Variants of the Invention

The Val54 variants may be constructed by standard techniques known in the art, including Site-directed mutagenesis as described, e.g., by Morinaga et al.,(1984), Biotechnology 2, p. 646–639, and in U.S. Pat. No. 4,760,025. Another suitable method introducing mutations into α-amylase-encoding DNA sequences is described in Nelson and Long, (1989), Analytical Biochemistry 180, p. 147–151. This method involves a 3-step generation of a PCR fragment containing the desired mutation introduced by using a chemical synthesized DNA strand as one primer in the PCR reaction. From the PCR-generated fragment, a DNA fragment carrying the mutation may be isolated by cleavage with restriction endonuclease and reinserted into an expression plasmid.

A Val54 variant may be expressed by cultivating a microorganism comprising a DNA sequence encoding the variant under conditions which are conducive for producing the variant. The variant may then subsequently be recovered from the resulting culture broth. Other methods known in the art may also be used. For instance WO 97/41213 discloses a suitable method for providing Val54 variants.

The invention also relates to a glucose syrup obtainable by the process of the invention as described above and illustrated below in the Examples section. Further, an aspect the invention also relates to the use of the glucose syrup obtainable by the process of the invention as ingredient in food products such as hard boiled candy, toffees, fudge, fondant and the like.

In another aspect the invention relates to the use of a Termamyl-like α-amylase with a substitution in position Val54 using SEQ ID NO: 2 as the backbone or a corresponding position in another Termamyl-like α-amylase for preparing a glucose syrup. The Termamyl-like variant may be any of the above mentioned.

MATERIALS AND METHODS

Materials

Enzyme:

Termamyl® from Novo Nordisk shown in SEQ ID NO: 2 substituted in position Val54Trp. The variant may be prepared as described in WO 97/41213.

Other Materials

Waxy maize starch from Cerestar.

METHODS

DE Determination

DE (dextrose equivalent is defined as the amount of reducing carbohydrate (measured as dextrose-equivalents) in a sample expressed as w/w % of the total amount of dissolved dry matter). It is measured by the neocuproine assay (Dygert, Li Floridana(1965) Anal. Biochem. No 368). The principle of the neocuproine assay is that $CuSO_4$ is added to the sample, $Cu^{++}$ is reduced by the reducing sugar and the formed neocuproine complex is measured at 450 nm.

General Molecular Biology Methods

DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

EXAMPLES

Example 1

Preparation of Glucose Syrup of the Acid Converted-type Enzymatically

A glucose syrup was prepared by treating a starch slurry containing 30% DS (30% Dry Solid) waxy maize starch, 40 ppm $Ca^{2+}$ (adding as $CaCl_2$) at pH 6.0 with 0.1 mg enzyme protein/g DS of Val54Trp substituted *Bacillus licheniformis* α-amylase. The temperature was kept at 95° C. for one hour and 80° C. for 72 hours.

The sugar profile of the prepared glucose syrup after 20 and 72 hours of treatment is shown in the Table 1 below:

TABLE 1

Sugar profile after 20 and 72 hours of treatment with V54W substituted *Bacillus licheniformis* α-amylase. The DE of the obtained syrup is also given

| | Time (Hours) | |
|---|---|---|
| % DPX on DS | 20 | 72 |
| DP1 | 7.9 | 10.1 |
| DP2 | 19.1 | 23.2 |
| DP3 | 14.3 | 14.0 |
| DP4 | 8.6 | 7.6 |
| DP5 | 8.5 | 6.6 |
| DP6 | 2.4 | 2.4 |
| DP7 | 3.1 | 4.1 |
| DP8 | 3.1 | 3.4 |
| DP9 | 2.5 | 2.4 |
| DP10+ | 30.5 | 26.4 |
| DE | 35 | 43 |

FIG. 3 shows the sugar spectrum of the glucose syrup obtained by treating a pre-cooked 5% Waxy maize starch substrate with a Val54Trp substituted *Bacillus licheniformis* α-amylase at 60° C. for 24 hours. FIG. 2 shows the sugar spectrum of a similar substrate treated with the native *Bacillus licheniformis* α-amylase under similar conditions.

What is claimed is:

1. A process for producing a glucose syrup, comprising treating a starch with a variant of an α-amylase, wherein the variant comprises a substitution of valine at position 54 with tryptophan, numbered according to the amino acid sequence of SEQ ID NO:2, wherein (a) the α-amylase has an amino acid sequence that is at least 60% homologous with SEQ ID NO:2, (b) the glucose syrup has a dextrose equivalent in the range of 35 to 45, (c) homology is determined by the gap programme from the GCG package version 7.3 (June 1993) using a gap creation penalty of 3.0 and gap extension penalty of 0.1; and (d) alignment is performed using the Pile Up programme from the GCG package using a gap creation penalty of 3.0 and gap extension penalty of 0.1.

2. The process of claim 1, wherein the dextrose equivalent is in the range of 35 to 42.

3. The process of claim 1, wherein the dextrose equivalent is about 42.

4. The process of claim 1, wherein the amylase has an amino acid sequence that is at least 70% homologous with SEQ ID NO:2.

5. The process of claim 4, wherein the amylase has an amino acid sequence that is at least 80% homologous with SEQ ID NO:2.

6. The process of claim 5, wherein the amylase has an amino acid sequence that is at least 90% homologous with SEQ ID NO:2.

7. The process of claim 6, wherein the amylase has an amino acid sequence that is at least 95% homologous with SEQ ID NO:2.

8. The process of claim 1, wherein the amylase has an amino acid sequence of SEQ ID NO:2.

9. The process of claim 1, wherein the amylase has an amino acid sequence of SEQ ID NO:3.

10. The process of claim 1, wherein the amylase has an amino acid sequence of SEQ ID NO:5.

11. The process of claim 1, wherein the amylase has an amino acid sequence of SEQ ID NO:6.

12. The process of claim 1, wherein the amylase has an amino acid sequence of SEQ ID NO:7.

13. The process of claim 1, wherein the amylase has an amino acid sequence of SEQ ID NO:8.

14. The process of claim 1, wherein the starch is treated with the variant for 20 to 100 hours.

15. The process of claim 14, wherein the starch is treated with the variant for 50–80 hours.

16. The process of claim 15, wherein the starch is treated with the variant for 60–75 hours.

* * * * *

SEQUENCE LISTING

```
<160> NUMBER OF SEQ ID NOS: 8

<210> SEQ ID NO 1
<211> LENGTH: 1912
<212> TYPE: DNA
<213> ORGANISM: Bacillus licheniformis
<220> FEATURE:
<221> NAME/KEY: CDS
<222> LOCATION: (421)...(1872)
```

```
<221> NAME/KEY: mat_peptide
<222> LOCATION: (421)...(1869)

<400> SEQUENCE: 1
cggaagattg gaagtacaaa ataagcaaa agattgtcaa tcatgtcatg agccatgcgg      60
gagacggaaa atcgtctta atgcacgata tttatgcaac gttcgcagat gctgctgaag     120
agattattaa aaagctgaaa gcaaaaggct atcaattggt aactgtatct cagcttgaag    180
aagtgaagaa gcagagaggc tattgaataa atgagtagaa gcgccatatc ggcgcttttc    240
ttttggaaga aatatagg  aaaatggtac ttgttaaaaa ttcggaatat ttatacaaca     300
tcatatgttt cacattgaaa ggggaggaga atcatgaaac aacaaaaacg gctttacgcc    360
cgattgctga cgctgttatt tgcgctcatc ttcttgctgc ctcattctgc agcagcggcg    420 gca aat ctt aat ggg acg ctg atg cag tat ttt gaa tgg tac atg ccc     468
Ala Asn Leu Asn Gly Thr Leu Met Gln Tyr Phe Glu Trp Tyr Met Pro
 1               5                  10                  15 aat gac ggc caa cat tgg agg cgt ttg caa aac gac tcg gca tat ttg     516
Asn Asp Gly Gln His Trp Arg Arg Leu Gln Asn Asp Ser Ala Tyr Leu
            20                  25                  30 gct gaa cac ggt att act gcc gtc tgg att ccc ccg gca tat aag gga     564
Ala Glu His Gly Ile Thr Ala Val Trp Ile Pro Pro Ala Tyr Lys Gly
        35                  40                  45 acg agc caa gcg gat gtg ggc tac ggt gct tac gac ctt tat gat tta     612
Thr Ser Gln Ala Asp Val Gly Tyr Gly Ala Tyr Asp Leu Tyr Asp Leu
    50                  55                  60 ggg gag ttt cat caa aaa ggg acg gtt cgg aca aag tac ggc aca aaa     660
Gly Glu Phe His Gln Lys Gly Thr Val Arg Thr Lys Tyr Gly Thr Lys
65                  70                  75                  80 gga gag ctg caa tct gcg atc aaa agt ctt cat tcc cgc gac att aac     708
Gly Glu Leu Gln Ser Ala Ile Lys Ser Leu His Ser Arg Asp Ile Asn
                85                  90                  95 gtt tac ggg gat gtg gtc atc aac cac aaa ggc ggc gct gat gcg acc     756
Val Tyr Gly Asp Val Val Ile Asn His Lys Gly Gly Ala Asp Ala Thr
            100                 105                 110 gaa gat gta acc gcg gtt gaa gtc gat ccc gct gac cgc aac cgc gta     804
Glu Asp Val Thr Ala Val Glu Val Asp Pro Ala Asp Arg Asn Arg Val
        115                 120                 125 att tca gga gaa cac cta att aaa gcc tgg aca cat ttt cat ttt ccg     852
Ile Ser Gly Glu His Leu Ile Lys Ala Trp Thr His Phe His Phe Pro
    130                 135                 140 ggg cgc ggc agc aca tac agc gat ttt aaa tgg cat tgg tac cat ttt     900
Gly Arg Gly Ser Thr Tyr Ser Asp Phe Lys Trp His Trp Tyr His Phe
145                 150                 155                 160 gac gga acc gat tgg gac gag tcc cga aag ctg aac cgc atc tat aag     948
Asp Gly Thr Asp Trp Asp Glu Ser Arg Lys Leu Asn Arg Ile Tyr Lys
                165                 170                 175 ttt caa gga aag gct tgg gat tgg gaa gtt tcc aat gaa aac ggc aac     996
Phe Gln Gly Lys Ala Trp Asp Trp Glu Val Ser Asn Glu Asn Gly Asn
            180                 185                 190 tat gat tat ttg atg tat gcc gac atc gat tat gac cat cct gat gtc    1044
Tyr Asp Tyr Leu Met Tyr Ala Asp Ile Asp Tyr Asp His Pro Asp Val
        195                 200                 205 gca gca gaa att aag aga tgg ggc act tgg tat gcc aat gaa ctg caa    1092
Ala Ala Glu Ile Lys Arg Trp Gly Thr Trp Tyr Ala Asn Glu Leu Gln
    210                 215                 220 ttg gac ggt ttc cgt ctt gat gct gtc aaa cac att aaa ttt tct ttt    1140
Leu Asp Gly Phe Arg Leu Asp Ala Val Lys His Ile Lys Phe Ser Phe
225                 230                 235                 240
```

```
ttg cgg gat tgg gtt aat cat gtc agg gaa aaa acg ggg aag gaa atg    1188
Leu Arg Asp Trp Val Asn His Val Arg Glu Lys Thr Gly Lys Glu Met
            245                 250                 255 ttt acg gta gct gaa tat tgg cag aat gac ttg ggc gcg ctg gaa aac    1236
Phe Thr Val Ala Glu Tyr Trp Gln Asn Asp Leu Gly Ala Leu Glu Asn
        260                 265                 270 tat ttg aac aaa aca aat ttt aat cat tca gtg ttt gac gtg ccg ctt    1284
Tyr Leu Asn Lys Thr Asn Phe Asn His Ser Val Phe Asp Val Pro Leu
    275                 280                 285 cat tat cag ttc cat gct gca tcg aca cag gga ggc ggc tat gat atg    1332
His Tyr Gln Phe His Ala Ala Ser Thr Gln Gly Gly Gly Tyr Asp Met
290                 295                 300 agg aaa ttg ctg aac ggt acg gtc gtt tcc aag cat ccg ttg aaa tcg    1380
Arg Lys Leu Leu Asn Gly Thr Val Val Ser Lys His Pro Leu Lys Ser
305                 310                 315                 320 gtt aca ttt gtc gat aac cat gat aca cag ccg ggg caa tcg ctt gag    1428
Val Thr Phe Val Asp Asn His Asp Thr Gln Pro Gly Gln Ser Leu Glu
        325                 330                 335 tcg act gtc caa aca tgg ttt aag ccg ctt gct tac gct ttt att ctc    1476
Ser Thr Val Gln Thr Trp Phe Lys Pro Leu Ala Tyr Ala Phe Ile Leu
    340                 345                 350 aca agg gaa tct gga tac cct cag gtt ttc tac ggg gat atg tac ggg    1524
Thr Arg Glu Ser Gly Tyr Pro Gln Val Phe Tyr Gly Asp Met Tyr Gly
355                 360                 365 acg aaa gga gac tcc cag cgc gaa att cct gcc ttg aaa cac aaa att    1572
Thr Lys Gly Asp Ser Gln Arg Glu Ile Pro Ala Leu Lys His Lys Ile
370                 375                 380 gaa ccg atc tta aaa gcg aga aaa cag tat gcg tac gga gca cag cat    1620
Glu Pro Ile Leu Lys Ala Arg Lys Gln Tyr Ala Tyr Gly Ala Gln His
385                 390                 395                 400 gat tat ttc gac cac cat gac att gtc ggc tgg aca agg gaa ggc gac    1668
Asp Tyr Phe Asp His His Asp Ile Val Gly Trp Thr Arg Glu Gly Asp
                405                 410                 415 agc tcg gtt gca aat tca ggt ttg gcg gca tta ata aca gac gga ccc    1716
Ser Ser Val Ala Asn Ser Gly Leu Ala Ala Leu Ile Thr Asp Gly Pro
            420                 425                 430 ggt ggg gca aag cga atg tat gtc ggc cgg caa aac gcc ggt gag aca    1764
Gly Gly Ala Lys Arg Met Tyr Val Gly Arg Gln Asn Ala Gly Glu Thr
        435                 440                 445 tgg cat gac att acc gga aac cgt tcg gag ccg gtt gtc atc aat tcg    1812
Trp His Asp Ile Thr Gly Asn Arg Ser Glu Pro Val Val Ile Asn Ser
    450                 455                 460 gaa ggc tgg gga gag ttt cac gta aac ggc ggg tcg gtt tca att tat    1860
Glu Gly Trp Gly Glu Phe His Val Asn Gly Gly Ser Val Ser Ile Tyr
465                 470                 475                 480 gtt caa aga tag aagagcagag aggacggatt tcctgaagga aatccgtttt        1912
Val Gln Arg
```

<210> SEQ ID NO 2
<211> LENGTH: 483
<212> TYPE: PRT
<213> ORGANISM: Bacillus licheniformis

<400> SEQUENCE: 2

```
Ala Asn Leu Asn Gly Thr Leu Met Gln Tyr Phe Glu Trp Tyr Met Pro
 1               5                  10                  15

Asn Asp Gly Gln His Trp Arg Arg Leu Gln Asn Asp Ser Ala Tyr Leu
                20                  25                  30

Ala Glu His Gly Ile Thr Ala Val Trp Ile Pro Pro Ala Tyr Lys Gly
            35                  40                  45
```

-continued

```
Thr Ser Gln Ala Asp Val Gly Tyr Gly Ala Tyr Asp Leu Tyr Asp Leu
    50                  55                  60
Gly Glu Phe His Gln Lys Gly Thr Val Arg Thr Lys Tyr Gly Thr Lys
65                  70                  75                  80
Gly Glu Leu Gln Ser Ala Ile Lys Ser Leu His Ser Arg Asp Ile Asn
                85                  90                  95
Val Tyr Gly Asp Val Val Ile Asn His Lys Gly Gly Ala Asp Ala Thr
                100                 105                 110
Glu Asp Val Thr Ala Val Glu Val Asp Pro Ala Asp Arg Asn Arg Val
                115                 120                 125
Ile Ser Gly Glu His Leu Ile Lys Ala Trp Thr His Phe His Phe Pro
    130                 135                 140
Gly Arg Gly Ser Thr Tyr Ser Asp Phe Lys Trp His Trp Tyr His Phe
145                 150                 155                 160
Asp Gly Thr Asp Trp Asp Glu Ser Arg Lys Leu Asn Arg Ile Tyr Lys
                165                 170                 175
Phe Gln Gly Lys Ala Trp Asp Trp Glu Val Ser Asn Glu Asn Gly Asn
                180                 185                 190
Tyr Asp Tyr Leu Met Tyr Ala Asp Ile Asp Tyr Asp His Pro Asp Val
                195                 200                 205
Ala Ala Glu Ile Lys Arg Trp Gly Thr Trp Tyr Ala Asn Glu Leu Gln
    210                 215                 220
Leu Asp Gly Phe Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                245                 250                 255
Phe Thr Val Ala Glu Tyr Trp Gln Asn Asp Leu Gly Ala Leu Glu Asn
                260                 265                 270
Tyr Leu Asn Lys Thr Asn Phe Asn His Ser Val Phe Asp Val Pro Leu
    275                 280                 285
His Tyr Gln Phe His Ala Ala Ser Thr Gln Gly Gly Gly Tyr Asp Met
    290                 295                 300
Arg Lys Leu Leu Asn Gly Thr Val Val Ser Lys His Pro Leu Lys Ser
305                 310                 315                 320
Val Thr Phe Val Asp Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
                340                 345                 350
Thr Arg Glu Ser Gly Tyr Pro Gln Val Phe Tyr Gly Asp Met Tyr Gly
                355                 360                 365
Thr Lys Gly Asp Ser Gln Arg Glu Ile Pro Ala Leu Lys His Lys Ile
    370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
                405                 410                 415
Ser Ser Val Ala Asn Ser Gly Leu Ala Ala Leu Ile Thr Asp Gly Pro
                420                 425                 430
Gly Gly Ala Lys Arg Met Tyr Val Gly Arg Gln Asn Ala Gly Glu Thr
                435                 440                 445
Trp His Asp Ile Thr Gly Asn Arg Ser Glu Pro Val Val Ile Asn Ser
    450                 455                 460
```

```
Glu Gly Trp Gly Glu Phe His Val Asn Gly Gly Ser Val Ser Ile Tyr
465                 470                 475                 480

Val Gln Arg

<210> SEQ ID NO 3
<211> LENGTH: 2604
<212> TYPE: DNA
<213> ORGANISM: Bacillus amyloliquefaciens

<400> SEQUENCE: 3
aagcttcaag cggtcaatcg gaatgtgcat ctcgcttcat acttaggttt tcacccgcat      60
attaagcagg cgttttttgaa ccgtgtgaca gaagctgttc gaaacccggg cgggcggttt    120
gattttaagg ggggacagta tgctgcctct tcacattaat ctcagcggaa aaagaatcat    180
cattgctggc gggggcaatg ttgcattaag aaggctgaaa cggtgtttcc ggaaggcgct    240
gatattaccg tgatcagtct gagcctgcct gaaattaaaa agctggcgga tgaaggacgc    300
atccgctgga ttccccggag aattgaaatg aaagatctca gcccgctttt tttcattatt    360
gccgcgacaa atgaccgagg cgtgaatcag agatatagccg caaacgcttc tgaaacgcag    420
ctggtcaact gtgtaagcaa ggctgaacaa ggcagcgtat atatgccgaa gatcatccgc    480
aaagggcgca ttcaagtatc agtatcaaca agcggggcaa gccccgcaca tacgaaaaga    540
ctggctgaaa acattgagcc tttgatgact gatgatttgg ctgaagaagt ggatcgattg    600
tttgagaaaa gaagaagacc ataaaaaatac cttgtctgtc atcagacagg gtatttttta    660
tgctgtccag actgtccgct gtgtaaaaaa taggaataaa ggggggttgt tattattta    720 ctgatatgta aaatataatt tgtataagaa atgagaggg agaggaaaca tgattcaaaa    780
acgaaagcgg acagtttcgt tcagacttgt gcttatgtgc acgctgttat ttgtcagttt    840
gccgattaca aaaacatcag ccgtaaatgg cacgctgatg cagtattttg aatggtatac    900
gccgaacgac ggccagcatt ggaaacgatt gcagaatgat gcggaacatt tatcggatat    960
cggaatcact gccgtctgga ttcctcccgc atacaaagga ttgagccaat ccgataacgg   1020
atacggacct tatgatttgt atgatttagg agaattccag caaaagggga cggtcagaac   1080
gaaatacggc acaaaatcag agcttcaaga tgcgatcggc tcactgcatt cccggaacgt   1140
ccaagtatac ggagatgtgg ttttgaatca taaggctggt gctgatgcaa cagaagatgt   1200
aactgccgtc gaagtcaatc cggccaatag aaatcaggaa acttcggagg aatatcaaat   1260
caaagcgtgg acgcattttc gttttccggg ccgtggaaac acgtacagtg atttttaaatg   1320 gcattggtat catttcgacg gagcggactg ggatgaatcc cggaagatca gccgcatctt   1380
taagtttcgt ggggaaggaa aagcgtggga ttgggaagta tcaagtgaaa acggcaacta   1440
tgactattta atgtatgctg atgttgacta cgaccaccct gatgtcgtgg cagagacaaa   1500
aaaatggggt atctggtatg cgaatgaact gtcattagac ggcttccgta ttgatgccgc   1560
caaacatatt aaattttcat ttctgcgtga ttgggttcag gcggtcagac aggcgacggg   1620
aaaagaaatg tttacggttg cggagtattg gcagaataat gccgggaaac tcgaaaacta   1680
cttgaataaa acaagcttta atcaatccgt gtttgatgtt ccgcttcatt tcaatttaca   1740
ggcggcttcc tcacaaggag gcggatatga tatgaggcgt ttgctggacg gtaccgttgt   1800
gtccaggcat ccggaaaagg cggttacatt tgttgaaaat catgacacac agccgggaca   1860
gtcattggaa tcgacagtcc aaacttggtt taaaccgctt gcatacgcct ttattttgac   1920
aagagaatcc ggttatcctc aggtgttcta tggggatatg tacgggacaa aagggacatc   1980
```

-continued

```
gccaaaggaa attccctcac tgaaagataa tatagagccg attttaaaag cgcgtaagga    2040
gtacgcatac gggccccagc acgattatat tgaccacccg gatgtgatcg gatggacgag    2100
ggaaggtgac agctccgccg ccaaatcagg tttggccgct taatcacgg acggacccgg     2160 cggatcaaag cggatgtatg ccggcctgaa aaatgccggc gagacatggt atgacataac    2220
gggcaaccgt tcagatactg taaaaatcgg atctgacggc tggggagagt ttcatgtaaa    2280
cgatgggtcc gtctccattt atgttcagaa ataaggtaat aaaaaaacac ctccaagctg    2340
agtgcgggta tcagcttgga ggtgcgttta ttttttcagc cgtatgacaa ggtcggcatc    2400
aggtgtgaca atacggtat gctggctgtc ataggtgaca atccggtt ttgcgccgtt       2460 tggcttttc acatgtctga tttttgtata atcaacaggc acggagccgg aatctttcgc    2520
cttggaaaaa taagcggcga tcgtagctgc ttccaatatg gattgttcat cgggatcgct    2580
gcttttaatc acaacgtggg atcc                                          2604
```

<210> SEQ ID NO 4
<211> LENGTH: 514
<212> TYPE: PRT
<213> ORGANISM: Bacillus amyloliquefaciens

<400> SEQUENCE: 4

```
Met Ile Gln Lys Arg Lys Arg Thr Val Ser Phe Arg Leu Val Leu Met
 1               5                  10                  15

Cys Thr Leu Leu Phe Val Ser Leu Pro Ile Thr Lys Thr Ser Ala Val
            20                  25                  30

Asn Gly Thr Leu Met Gln Tyr Phe Glu Trp Tyr Thr Pro Asn Asp Gly
        35                  40                  45

Gln His Trp Lys Arg Leu Gln Asn Asp Ala Glu His Leu Ser Asp Ile
    50                  55                  60

Gly Ile Thr Ala Val Trp Ile Pro Pro Ala Tyr Lys Gly Leu Ser Gln
65                  70                  75                  80

Ser Asp Asn Gly Tyr Gly Pro Tyr Asp Leu Tyr Asp Leu Gly Glu Phe
                85                  90                  95

Gln Gln Lys Gly Thr Val Arg Thr Lys Tyr Gly Thr Lys Ser Glu Leu
            100                 105                 110

Gln Asp Ala Ile Gly Ser Leu His Ser Arg Asn Val Gln Val Tyr Gly
        115                 120                 125

Asp Val Val Leu Asn His Lys Ala Gly Ala Asp Ala Thr Glu Asp Val
    130                 135                 140

Thr Ala Val Glu Val Asn Pro Ala Asn Arg Asn Gln Glu Thr Ser Glu
145                 150                 155                 160

Glu Tyr Gln Ile Lys Ala Trp Thr Asp Phe Arg Phe Pro Gly Arg Gly
                165                 170                 175

Asn Thr Tyr Ser Asp Phe Lys Trp His Trp Tyr His Phe Asp Gly Ala
            180                 185                 190

Asp Trp Asp Glu Ser Arg Lys Ile Ser Arg Ile Phe Lys Phe Arg Gly
        195                 200                 205

Glu Gly Lys Ala Trp Asp Trp Glu Val Ser Ser Glu Asn Gly Asn Tyr
    210                 215                 220

Asp Tyr Leu Met Tyr Ala Asp Val Asp Tyr Asp His Pro Asp Val Val
225                 230                 235                 240

Ala Glu Thr Lys Lys Trp Gly Ile Trp Tyr Ala Asn Glu Leu Ser Leu
                245                 250                 255

Asp Gly Phe Arg Ile Asp Ala Ala Lys His Ile Lys Phe Ser Phe Leu
```

```
                     260                 265                 270
Arg Asp Trp Val Gln Ala Val Arg Gln Ala Thr Gly Lys Glu Met Phe
            275                 280                 285
Thr Val Ala Glu Tyr Trp Gln Asn Asn Ala Gly Lys Leu Glu Asn Tyr
    290                 295                 300
Leu Asn Lys Thr Ser Phe Asn Gln Ser Val Phe Asp Val Pro Leu His
305                 310                 315                 320
Phe Asn Leu Gln Ala Ala Ser Ser Gln Gly Gly Gly Tyr Asp Met Arg
                325                 330                 335
Arg Leu Leu Asp Gly Thr Val Val Ser Arg His Pro Glu Lys Ala Val
            340                 345                 350
Thr Phe Val Glu Asn His Asp Thr Gln Pro Gly Gln Ser Leu Glu Ser
        355                 360                 365
Thr Val Gln Thr Trp Phe Lys Pro Leu Ala Tyr Ala Phe Ile Leu Thr
    370                 375                 380
Arg Glu Ser Gly Tyr Pro Gln Val Phe Tyr Gly Asp Met Tyr Gly Thr
385                 390                 395                 400
Lys Gly Thr Ser Pro Lys Glu Ile Pro Ser Leu Lys Asp Asn Ile Glu
                405                 410                 415
Pro Ile Leu Lys Ala Arg Lys Glu Tyr Ala Tyr Gly Pro Gln His Asp
            420                 425                 430
Tyr Ile Asp His Pro Asp Val Ile Gly Trp Thr Arg Glu Gly Asp Ser
        435                 440                 445
Ser Ala Ala Lys Ser Gly Leu Ala Ala Leu Ile Thr Asp Gly Pro Gly
    450                 455                 460
Gly Ser Lys Arg Met Tyr Ala Gly Leu Lys Asn Ala Gly Glu Thr Trp
465                 470                 475                 480
Tyr Asp Ile Thr Gly Asn Arg Ser Asp Thr Val Lys Ile Gly Ser Asp
                485                 490                 495
Gly Trp Gly Glu Phe His Val Asn Asp Gly Ser Val Ser Ile Tyr Val
            500                 505                 510
Gln Lys

<210> SEQ ID NO 5
<211> LENGTH: 485
<212> TYPE: PRT
<213> ORGANISM: Bacillus

<400> SEQUENCE: 5

His His Asn Gly Thr Asn Gly Thr Met Met Gln Tyr Phe Glu Trp His
  1               5                  10                  15
Leu Pro Asn Asp Gly Asn His Trp Asn Arg Leu Arg Asp Asp Ala Ser
                20                  25                  30
Asn Leu Arg Asn Arg Gly Ile Thr Ala Ile Trp Ile Pro Pro Ala Trp
            35                  40                  45
Lys Gly Thr Ser Gln Asn Asp Val Gly Tyr Gly Ala Tyr Asp Leu Tyr
    50                  55                  60
Asp Leu Gly Glu Phe Asn Gln Lys Gly Thr Val Arg Thr Lys Tyr Gly
65                  70                  75                  80
Thr Arg Ser Gln Leu Glu Ser Ala Ile His Ala Leu Lys Asn Asn Gly
                85                  90                  95
Val Gln Val Tyr Gly Asp Val Val Met Asn His Lys Gly Gly Ala Asp
                100                 105                 110
Ala Thr Glu Asn Val Leu Ala Val Glu Val Asn Pro Asn Asn Arg Asn
```

```
                    115                 120                 125
Gln Glu Ile Ser Gly Asp Tyr Thr Ile Glu Ala Trp Thr Lys Phe Asp
            130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
            195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
            275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 6
<211> LENGTH: 400
<212> TYPE: PRT
<213> ORGANISM: Bacillus

<400> SEQUENCE: 6
```

```
Asn Gly Thr Asn Gly Thr Met Met Gln Tyr Phe Glu Trp Tyr Leu Pro
 1               5                  10                  15

Asn Asp Gly Asn His Trp Asn Arg Leu Arg Ser Asp Ala Ser Asn Leu
            20                  25                  30

Lys Asp Lys Gly Ile Ser Ala Val Trp Ile Pro Pro Ala Trp Lys Gly
        35                  40                  45

Ala Ser Gln Asn Asp Val Gly Tyr Gly Ala Tyr Asp Leu Tyr Asp Leu
50                  55                  60

Gly Glu Phe Asn Gln Lys Gly Thr Ile Arg Thr Lys Tyr Gly Thr Arg
65              70                  75                  80

Asn Gln Leu Gln Ala Ala Val Asn Ala Leu Lys Ser Asn Gly Ile Gln
                85                  90                  95

Val Tyr Gly Asp Val Val Met Asn His Lys Gly Ala Asp Ala Thr
                100                 105                 110

Glu Met Val Arg Ala Val Glu Val Asn Pro Asn Asn Arg Asn Gln Glu
            115                 120                 125

Val Ser Gly Glu Tyr Thr Ile Glu Ala Trp Thr Lys Phe Asp Phe Pro
130                 135                 140

Gly Arg Gly Asn Thr His Ser Asn Phe Lys Trp Arg Trp Tyr His Phe
145                 150                 155                 160

Asp Gly Val Asp Trp Asp Gln Ser Arg Lys Leu Asn Asn Arg Ile Tyr
                165                 170                 175

Lys Phe Arg Gly Asp Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ser Ile His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Asn Lys Thr Asn Trp Asn His Ser Val Phe Asp
        275                 280                 285

Val Pro Leu His Tyr Asn Phe Tyr Asn Ala Ser Lys Ser Gly Gly Asn
290                 295                 300

Tyr Asp Met Arg Gln Ile Phe Asn Gly Thr Val Val Gln Arg His Pro
305                 310                 315                 320

Met His Ala Val Thr Phe Val Asp Asn His Asp Ser Gln Pro Glu Glu
                325                 330                 335

Ala Leu Glu Ser Phe Val Glu Trp Phe Lys Pro Leu Ala Tyr Ala
            340                 345                 350

Leu Thr Leu Thr Arg Glu Gln Gly Tyr Pro Ser Val Phe Tyr Gly Asp
            355                 360                 365

Tyr Tyr Gly Ile Pro Thr His Gly Val Pro Ala Met Lys Ser Lys Ile
        370                 375                 380

Asp Pro Ile Leu Glu Ala Arg Gln Lys Tyr Ala Tyr Gly Arg Gln Asn
385                 390                 395                 400

<210> SEQ ID NO 7
<211> LENGTH: 485
<212> TYPE: PRT
```

<213> ORGANISM: Bacillus

<400> SEQUENCE: 7

```
His His Asn Gly Thr Asn Gly Thr Met Met Gln Tyr Phe Glu Trp Tyr
 1               5                  10                  15

Leu Pro Asn Asp Gly Asn His Trp Asn Arg Leu Arg Asp Asp Ala Ala
                20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
 65                 70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
        115                 120                 125

Gln Glu Thr Ser Gly Glu Tyr Ala Ile Glu Ala Trp Thr Lys Phe Asp
    130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile His Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Ala
        275                 280                 285

Phe Asp Val Pro Leu His Tyr Asn Leu Tyr Asn Ala Ser Asn Ser Gly
    290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Leu Leu Gln Ala Arg Gln Thr Phe Ala Tyr Gly Thr
385                 390                 395                 400
```

```
Gln His Asp Tyr Phe Asp His His Asp Ile Ile Gly Trp Thr Arg Glu
            405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
            435                 440                 445

Gln Val Trp Arg Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Val Trp Val Lys Gln
            485

<210> SEQ ID NO 8
<211> LENGTH: 514
<212> TYPE: PRT
<213> ORGANISM: Bacillus

<400> SEQUENCE: 8

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
            85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
            165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
            245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asp Gly Thr Met Ser Leu Phe Asp
        275                 280                 285
```

-continued

```
Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Gly
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp
```